(12) United States Patent
Katakura

(10) Patent No.: US 11,815,739 B2
(45) Date of Patent: Nov. 14, 2023

(54) ENDOSCOPE OPTICAL SYSTEM, ENDOSCOPE, IMAGE PICKUP UNIT AND ENDOSCOPE INSERTION DEVICE

(71) Applicant: OLYMPUS CORPORATION, Hachioji (JP)

(72) Inventor: Masahiro Katakura, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 493 days.

(21) Appl. No.: 17/089,773

(22) Filed: Nov. 5, 2020

(65) Prior Publication Data
US 2021/0199920 A1    Jul. 1, 2021

Related U.S. Application Data

(63) Continuation of application No. PCT/JP2019/006760, filed on Feb. 22, 2019.

(30) Foreign Application Priority Data

May 14, 2018    (JP) .................................. 2018-092751

(51) Int. Cl.
*G02B 9/12*    (2006.01)
*G02B 13/04*    (2006.01)
(Continued)

(52) U.S. Cl.
CPC ............... *G02B 9/12* (2013.01); *G02B 13/04* (2013.01); *G02B 23/2438* (2013.01); *H04N 23/55* (2023.01); *H04N 23/555* (2023.01)

(58) Field of Classification Search
CPC ........ G02B 9/12; G02B 13/04; G02B 23/243; G02B 13/0045; G02B 23/26; G02B 9/34;
(Continued)

(56) References Cited

U.S. PATENT DOCUMENTS 6,166,784 A    12/2000    Murata et al.
6,288,767 B1    9/2001    Murata et al.
(Continued)

FOREIGN PATENT DOCUMENTS

JP    H10073758 A    3/1998
JP    2011227351 A    11/2011
(Continued)

OTHER PUBLICATIONS

Gross, Handbook of Optical Systems, vol. 3: Aberration theory and correction of Optical Systems (Year: 2007).*
(Continued)

*Primary Examiner* — Marin Pichler
(74) *Attorney, Agent, or Firm* — Holtz, Holtz & Volek PC

(57)    ABSTRACT

An endoscope optical system includes, in order from an object side: a fixed negative first lens group; a movable positive second lens group; a fixed aperture stop; and a fixed positive third lens group, the endoscope optical system being capable of switching between a normal observation state and a magnified observation state by moving the second lens group along an optical axis, in which the third lens group includes, in order from the object side: a cemented lens consisted of three lenses; and a cemented lens consisted of two lenses. In the cemented lens consisted of three lenses, three lenses of a positive lens, a negative lens, and a positive lens are cemented. In the cemented lens consisted of two lenses, two lenses of a positive lens and a negative lens are cemented. The following conditional expressions (1) and (2) are satisfied: $1.70<(nd3G1+nd3G2+nd3G3)/3<2.0$ (1); and $1.72<(nd3G4+nd3G5)/2<2.0$ (2).

10 Claims, 5 Drawing Sheets

(51) Int. Cl.
*H04N 5/225* (2006.01)
*H04N 23/55* (2023.01)
*G02B 23/24* (2006.01)
*H04N 23/50* (2023.01)

(58) Field of Classification Search
CPC ........ G02B 15/1435; G02B 15/143507; G02B 23/2438; G02B 15/1445; G02B 7/04; G02B 21/0028; G02B 23/24; G02B 23/2407; G02B 23/2423; G02B 9/60; H04N 23/55; H04N 23/555; A61B 1/00; A61B 1/00163; A61B 1/04; A61B 1/05; A61B 1/00096; A61B 1/00188
USPC ........ 359/753, 754–792, 664, 676, 680–682, 359/686, 689, 748, 786–790; 600/101, 600/109, 160–182
See application file for complete search history.

(56) References Cited

U.S. PATENT DOCUMENTS

| | | | |
|---|---|---|---|
| 8,422,143 | B2 | 4/2013 | Saori |
| 2003/0214726 | A1* | 11/2003 | Mihara .................. G02B 13/04 359/689 |
| 2012/0044575 | A1 | 2/2012 | Saori |
| 2015/0268460 | A1* | 9/2015 | Takada .................. G02B 13/04 359/738 |
| 2017/0049306 | A1* | 2/2017 | Katakura ............... G02B 17/04 |
| 2019/0064501 | A1 | 2/2019 | Katakura |

FOREIGN PATENT DOCUMENTS

| | | |
|---|---|---|
| JP | 2012063756 A | 3/2012 |
| JP | 6279195 B1 | 1/2018 |
| WO | 2017183371 A1 | 10/2017 |
| WO | 2018008460 A1 | 1/2018 |

OTHER PUBLICATIONS

International Search Report (and English language translation thereof) dated May 21, 2019, issued in International Application No. PCT/JP2019/006760.

Written Opinion dated May 21, 2019, issued in International Application No. PCT/JP2019/006760.

International Preliminary Report on Patentability (IPRP) (and English language translation thereof) dated Nov. 26, 2020 issued in International Application No. PCT/JP2019/006760.

* cited by examiner

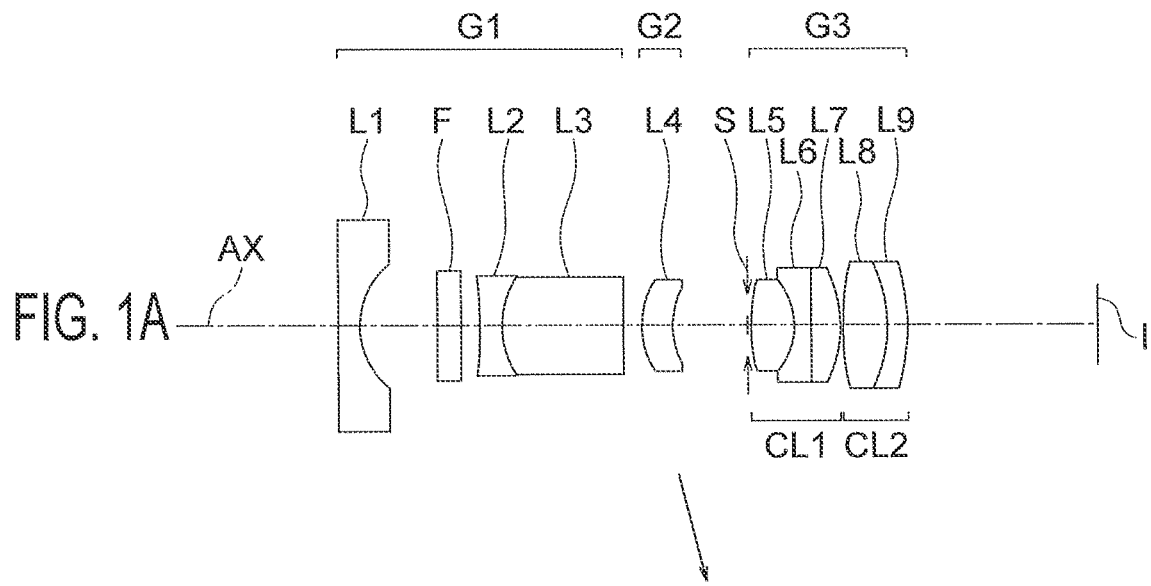
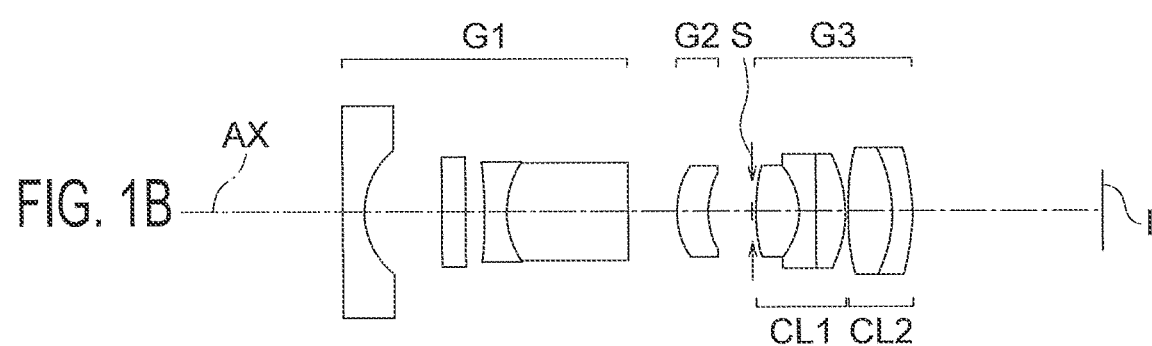

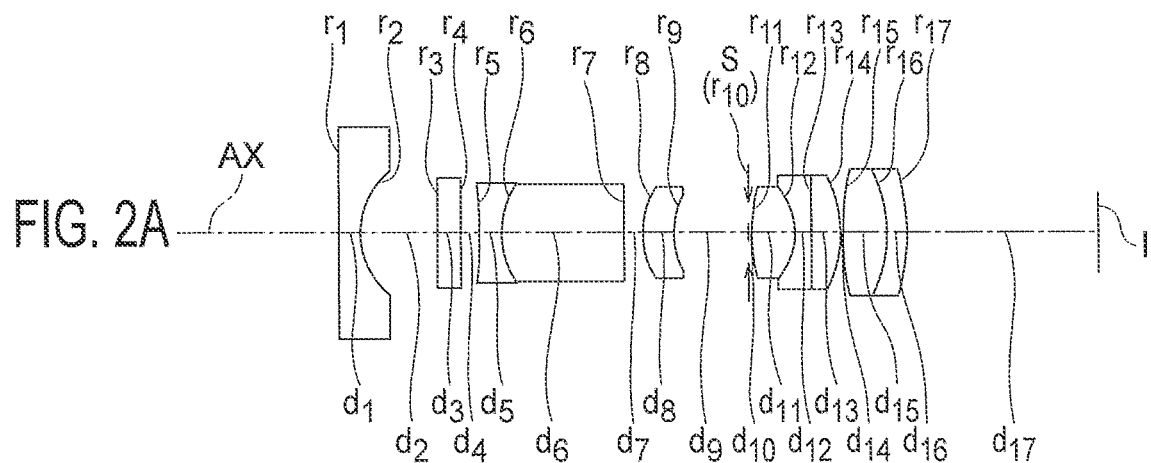
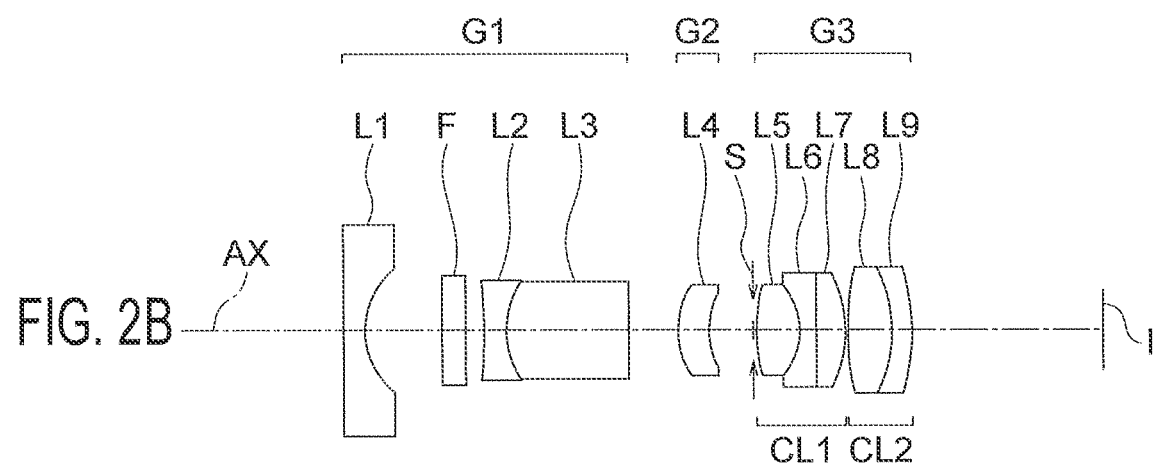

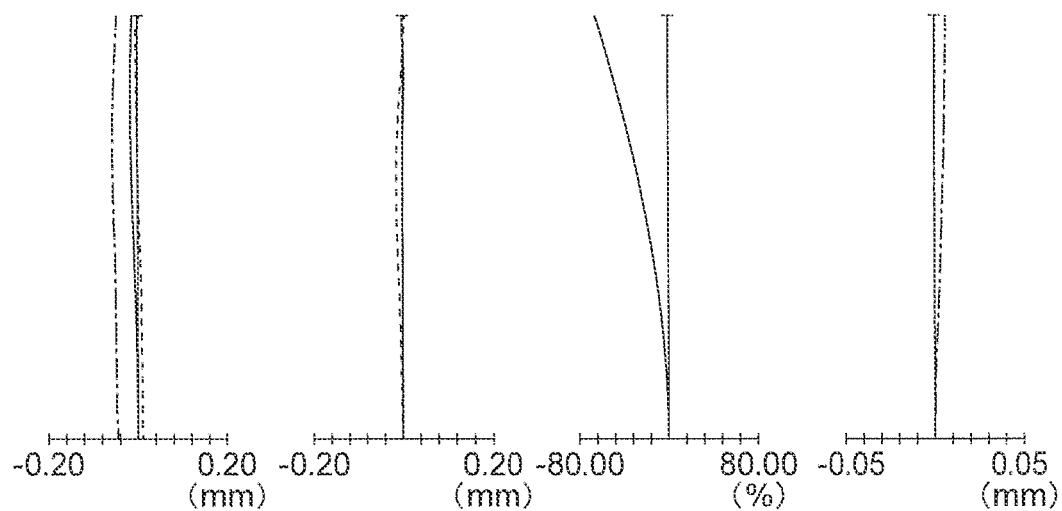

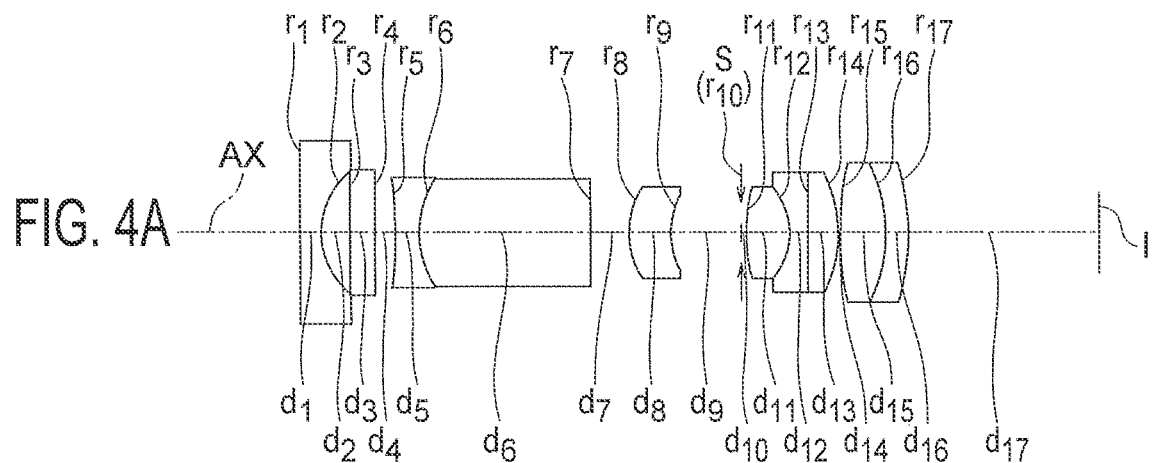
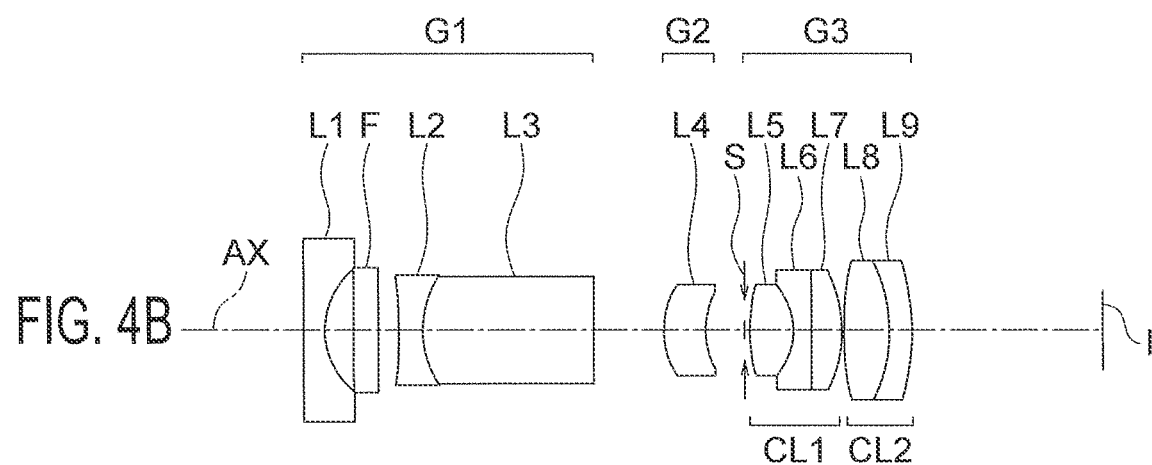

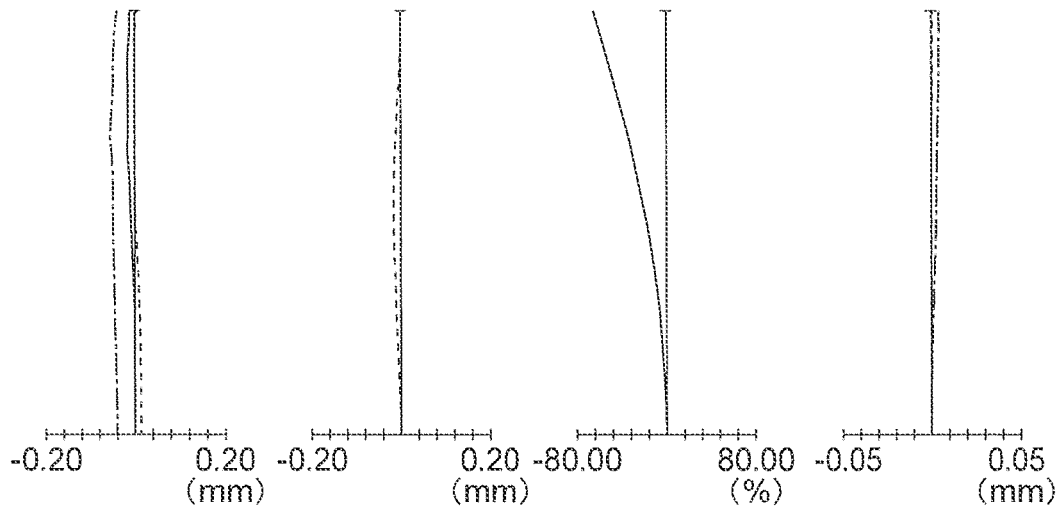

ENDOSCOPE OPTICAL SYSTEM, ENDOSCOPE, IMAGE PICKUP UNIT AND ENDOSCOPE INSERTION DEVICE

CROSS-REFERENCE TO RELATED APPLICATION

The present application is a continuation of PCT/JP2019/006760, filed on Feb. 22, 2019 which is based upon and claims the benefit of priority from Japanese Patent Application No. 2018-092751 filed on May 14, 2018; the entire contents of which are incorporated herein by reference.

BACKGROUND

Technical Field

The disclosure relates to an endoscope optical system, an endoscope, an image pickup unit, and an endoscope insertion device.

Description of the Related Art

An objective optical system described in Japanese Patent No. 6279195 is one of the objective optical systems for endoscopes. This objective optical system includes, in order from an object side: a first lens group having a negative refractive power; a second lens group having a positive refractive power; and a third lens group having a positive refractive power.

In this objective optical system, the second lens group moves along the optical axis, so that switching between normal observation and magnified observation mode is performed.

SUMMARY

An endoscope optical system according to at least some embodiments of the present disclosure includes, in order from an object side:
  a fixed negative first lens group; a movable positive second lens group; a fixed aperture stop; and a fixed positive third lens group,
  the endoscope optical system being capable of switching between a normal observation state and a magnified observation state by moving the second lens group along an optical axis, in which
  the third lens group includes, in order from the object side: a cemented lens consisted of three lenses; and a cemented lens consisted of two lenses,
  in the cemented lens consisted of three lenses, three lenses of a positive lens, a negative lens, and a positive lens are cemented,
  in the cemented lens consisted of two lenses, two lenses of a positive lens and a negative lens are cemented, and
  the following conditional expressions (1) and (2) are satisfied:

$$1.70 < (nd3G1 + nd3G2 + nd3G3)/3 < 2.0 \quad (1)$$

$$1.72 < (nd3G4 + nd3G5)/2 < 2.0 \quad (2)$$

where
  $nd3G1$ is a refractive index in d line of a lens nearest to the object side in the cemented lens consisted of the three lenses,
  $nd3G2$ is a refractive index in d line of a lens second nearest to the object side in the cemented lens consisted of the three lenses,
  $nd3G3$ is a refractive index in d line of a lens nearest to an image side in the cemented lens consisted of the three lenses,
  $nd3G4$ is a refractive index in d line of a lens nearest to the object side in the cemented lens consisted of the two lenses, and
  $nd3G5$ is a refractive index in d line of a lens nearest to the image side in the cemented lens consisted of the two lenses.

An endoscope according to at least some embodiments of the present disclosure includes the endoscope optical system described above.

An image pickup unit according to at least some embodiments of the present disclosure includes the endoscope optical system described above and an image pickup element configured to pick up an image formed by the endoscope optical system.

An endoscope insertion device according to at least some embodiments of the present disclosure includes the image pickup unit described above at a distal end thereof.

Hereinafter, the cemented lens consisted of three lenses is referred to as three-lens cemented lens, if necessary. The cemented lens consisted of two lenses is referred to as two-lens cemented lens, if necessary.

BRIEF DESCRIPTION OF THE DRAWINGS

FIG. 1A is a lens sectional view in a normal observation state of an endoscope optical system according to an embodiment, and FIG. 1B is a lens sectional view in a magnified observation state of the endoscope optical system according to the embodiment;

FIG. 2A is a lens sectional view in a normal observation state of an endoscope optical system according to Example 1, and FIG. 2B is a lens sectional view in a magnified observation state of the endoscope optical system according to Example 1;

FIG. 3A is a diagram illustrating spherical aberration (SA) in the normal observation state, FIG. 3B is a diagram illustrating astigmatism (AS) in the normal observation state, FIG. 3C is a diagram illustrating distortion (DT) in the normal observation state, and FIG. 3D is a diagram illustrating chromatic aberration of magnification (CC) in the normal observation state of the endoscope optical system according to Example 1;

FIG. 3E is a diagram illustrating spherical aberration (SA) in the magnified observation state, FIG. 3F is a diagram illustrating astigmatism (AS) in the magnified observation state, FIG. 3G is a diagram illustrating distortion (DT) in the magnified observation state, and FIG. 3H is a diagram illustrating chromatic aberration of magnification (CC) in the magnified observation state;

FIG. 4A is a lens sectional view in a normal observation state of an endoscope optical system according to Example 2, and FIG. 4B is a lens sectional view in a magnified observation state of the endoscope optical system according to Example 2;

FIG. 5A is a diagram illustrating spherical aberration (SA) in the normal observation state, FIG. 5B is a diagram illustrating astigmatism (A) in the normal observation state, FIG. 5C is a diagram illustrating distortion (DT) in the normal observation state, and FIG. 5D is a diagram illustrating chromatic aberration of magnification (CC) in the normal observation state of the endoscope optical system according to Example 2; and FIG. 5E is a diagram illustrating spherical aberration (SA) in the magnified observation state, FIG. 5F is a diagram illustrating astigmatism (AS) in the magnified observation state, FIG. 5G is a diagram illustrating distortion (DT) in the magnified observation state, and FIG. 5H is a diagram illustrating chromatic aberration of magnification (CC) in the magnified observation state.

DETAILED DESCRIPTION

An endoscope optical system, an endoscope, an image pickup unit, and an endoscope insertion device according to an embodiment will be explained in detail below based on the drawings. An objective optical system of an endoscope device is used as an example of the endoscope optical system. It should be noted that the present disclosure is not limited by this embodiment.

An endoscope optical system according to an embodiment will be explained in detail below based on the drawings. It should be noted that the present disclosure is not limited by this embodiment.

EMBODIMENT

FIG. 1A is a lens sectional view in a normal observation state of an endoscope optical system according to an embodiment. FIG. 1B is a lens sectional view in a close observation state of the endoscope optical system according to the embodiment. From the normal observation state to the close observation state, a second lens group G2 moves toward the image side.

The endoscope optical system according to the present embodiment includes, in order from an object side: a fixed negative first lens group G1; a movable positive second lens group G2; a fixed aperture stop S; and a fixed positive third lens group G3.

The endoscope optical system is capable of switching between a normal observation state and a magnified observation state by moving the second lens group G2 along an optical axis AX.

The third lens group G3 includes, in order from the object side: a three-lens cemented lens CL1 in which three lenses of a positive lens L5; a negative lens L6; and a positive lens L7 are cemented; and a two-lens cemented lens CL2 in which two lenses of a positive lens L8 and a negative lens L9 are cemented.

The following conditional expressions (1) and (2) are satisfied:

$$1.70 < (nd3G1 + nd3G2 + nd3G3)/3 < 2.0 \quad (1)$$

$$1.72 < (nd3G4 + nd3G5)/2 < 2.0 \quad (2)$$

where nd3G1 is the refractive index in d line of the lens L5 nearest to the object side in the three-lens cemented lens CL1 in the third lens group G3, nd3G2 is the refractive index in d line of the lens L6 second nearest to the object side in the three-lens cemented lens CL1 in the third lens group G3, nd3G3 is the refractive index in d line of the lens L7 nearest to an image side in the three-lens cemented lens CL1 in the third lens group G3, nd3G4 is the refractive index in d line of the lens L8 nearest to the object side in the two-lens cemented lens CL2 in the third lens group G3, and nd3G5 is the refractive index in d line of the lens L9 nearest to the image side in the two-lens cemented lens CL2 in the third lens group.

The reason and the operational effect of such a configuration in the endoscope optical system according to the present embodiment will be explained below. The endoscope optical system according to the present embodiment includes, in order from the object side: the negative first lens group G1; the positive second lens group G2 movable at a time of focusing; the aperture stop S; and the positive third lens group G3.

Because of such a configuration, it is possible to switch between the normal observation state and the magnified observation state. Then, the endoscope optical system according to the present embodiment is an optical system in which aberration variation at a time of focusing is small and which is robust against a manufacturing error, while a long back focus is ensured.

The third lens group G3 includes the three-lens cemented lens CL1 in which three lenses of the positive lens L5, the negative lens L6, and the positive lens L7 are cemented, in order from the object side, with no air space interposed.

Furthermore, the third lens group G3 includes the two-lens cemented lens CL2 in which two lenses of the positive lens L8 and the negative lens L9 are cemented with no air space interposed. Accordingly, it becomes possible to correct chromatic aberration and, in particular, it is possible to favorably correct longitudinal chromatic aberration.

The conditional expression (1) defines an appropriate refractive index of the three-lens cemented lens CL1. Within a range of the conditional expression (1), an appropriate refractive index is achieved, and therefore it is not necessary to impart an extremely strong curvature to each lens surface. Therefore, it is possible to favorably correct chromatic aberration and Seidel aberrations.

When the conditional expression (1) takes a value larger than the upper limit value thereof, the availability of a lens glass material becomes significantly worse. In this case, the manufacturing cost of lenses becomes high and therefore this is not preferable.

When the conditional expression (1) takes a value smaller than the lower limit value thereof, it is necessary to impart an extremely strong curvature to each lens surface in order to obtain a positive refractive power (power) necessary for the third lens group G3. Accordingly, it becomes impossible to favorably correct chromatic aberration and Seidel aberrations and therefore this is not preferable.

The conditional expression (2) defines an appropriate refractive index of the two-lens cemented lens CL2. Within a range of the conditional expression (2), an appropriate refractive index is achieved. In this case, it is not necessary to impart an excessively strong curvature to each lens surface. Accordingly, it is possible to favorably correct chromatic aberration and Seidel aberrations.

When the conditional expression (2) takes a value larger than the upper limit value thereof, the availability of a lens glass material becomes significantly worse. In this case, the manufacturing cost becomes high and therefore this is not preferable.

When the conditional expression (2) takes a value smaller than the lower limit value thereof, it is necessary to impart an extremely strong curvature to each lens surface in order to obtain a positive refractive power necessary for the third lens group G3. In this case, it becomes impossible to favorably correct chromatic aberration and Seidel aberrations and therefore this is not preferable.

It is desirable that the following conditional expression (1)' be satisfied instead of the conditional expression (1).

$$1.72 < (nd3G1 + nd3G2 + nd3G3)/3 < 1.85 \quad (1)'$$

Furthermore, it is more desirable that the following conditional expression (1)″ be satisfied instead of the conditional expression (1).

$$1.73 < (nd3G1 + nd3G2 + nd3G3)/3 < 1.80 \quad (1)''$$

Furthermore, it is more desirable that the following conditional expression (2)′ be satisfied instead of the conditional expression (2).

$$1.72 < (nd3G4 + nd3G5)/2 < 1.75 \quad (2)'$$

Accordingly, it is possible to correct chromatic aberration and Seidel aberrations more favorably.

The third lens group G3 of the endoscope optical system according to the present embodiment includes the three-lens cemented lens CL1 and the two-lens cemented lens CL2. In the three-lens cemented lens CL1, three lenses of the positive lens L5, the negative lens L6, and the positive lens L7 are cemented with no air and space interposed therebetween. In the two-lens cemented lens CL2, two lenses of the positive lens L8 and the negative lens L9 are cemented with no air and space interposed therebetween.

In this way, because of the cemented lenses bonded and fixed, it is possible to prevent shift movement of lenses due to low impact.

Furthermore, according to a preferable aspect of the present embodiment, it is desirable that the following conditional expression (3) be satisfied:

$$1.01 < \omega(\text{wide})/\omega(\text{tele}) < 5.0 \quad (3)$$

where
- ω(wide) is a half angle of view in the normal observation state of the endoscope optical system, and
- ω(tele) is a half angle of view in the magnified observation state of the endoscope optical system.

The conditional expression (3) is a conditional expression representing change in angle of view at a time of focusing. When the value of ω(wide)/ω(tele) is within a range of the conditional expression (3), it is possible to obtain an appropriate change in angle of view.

When the conditional expression (3) takes a value smaller than the lower limit value thereof, the configuration of the present embodiment becomes unnecessary.

When the conditional expression (3) takes a value larger than the upper limit value thereof, the change in angle of view is excessively large. Therefore, it is necessary to impart a large refractive power to the second lens group G2. As a result, the sensitivity to a lens manufacturing error becomes acute. That is, the influence of a lens manufacturing error is large and therefore this is not preferable.

It is desirable that the following conditional expression (3)′ be satisfied instead of the conditional expression (3).

$$1.02 < \omega(\text{wide})/\omega(\text{tele}) < 2.0 \quad (3)'$$

Furthermore, it is more desirable that the following conditional expression (3)″ be satisfied instead of the conditional expression (3).

$$1.03 < \omega(\text{wide})/\omega(\text{tele}) < 1.2 \quad (3)''$$

Accordingly, it is possible to obtain a more appropriate change in angle of view at a time of focusing.

Furthermore, according to a preferable aspect of the present embodiment, it is desirable that the following conditional expression (4) be satisfied:

$$0.8 < (R3G3\text{front} + R3G3\text{rear})/(R3G3\text{front} - R3G3\text{rear}) < 1.2 \quad (4)$$

where
- R3G3front is the radius of curvature on an object-side surface of the lens L7 nearest to the image side in the three-lens cemented lens CL1 in the third lens group G3, and
- R3G3rear is the radius of curvature on an image-side surface of the lens L7 nearest to the image side in the three-lens cemented lens CL1 in the third lens group G3.

The conditional expression (4) defines an appropriate shape factor for the lens L7 nearest to the image side in the three-lens cemented lens CL1 in the third lens group G3.

Within a range of the conditional expression (4), an appropriate lens shape is acquired and therefore, it is possible to favorably correct chromatic aberration and Seidel aberrations. When the conditional expression (4) takes a value larger than the upper limit value thereof or smaller than the lower limit value thereof, the curvature of the object-side surface of the lens or the image-side surface of the lens becomes extremely strong. In this case, it becomes impossible to favorably correct aberrations and therefore this is not preferable.

It is desirable that the following conditional expression (4)′ be satisfied instead of the conditional expression (4).

$$0.9 < (R3G3\text{front} + R3G3\text{rear})/(R3G3\text{front} - R3G3\text{rear}) < 1.1 \quad (4)'$$

Furthermore, it is more desirable that the following conditional expression (4)″ be satisfied instead of the conditional expression (4).

$$0.95 < (R3G3\text{front} + R3G3\text{rear})/(R3G3\text{front} - R3G3\text{rear}) < 1.05 \quad (4)''$$

Furthermore, according to a preferable aspect of the present embodiment, it is desirable that both of the following conditional expressions (5) and (6) be satisfied:

$$2.0 < DG31/DG32 < 3.5 \quad (5)$$

$$1.4 < DG33/DG32 < 1.9 \quad (6)$$

where
- DG31 is the lens center thickness of the lens L5 nearest to the object side in the three-lens cemented lens CL1 in the third lens group G3,
- DG32 is the lens center thickness of the lens L6 second nearest to the object side in the three-lens cemented lens CL1 in the third lens group G3, and
- DG33 is the lens center thickness of the lens L7 nearest to the image side in the three-lens cemented lens CL1 in the third lens group G3.

The conditional expression (5) defines an appropriate relation between the center thickness of the lens L5 nearest to the object side and the center thickness of the (middle) lens L6 second nearest to the object side in the three-lens cemented lens CL1 in the third lens group G3.

The conditional expression (6) defines an appropriate relation between the center thickness of the lens L7 nearest to the image side and the center thickness of the (middle) lens L6 second nearest to the object side in the three-lens cemented lens CL1 in the third lens group G3.

When the conditional expressions (5) and (6) take values smaller than the lower limit values thereof, the thickness of the positive (convex shape) lens L5 nearest to the object side or the thickness of the lens L7 nearest to the image side becomes small. Therefore, it is not preferable because it is impossible to ensure the edge thickness of the lens L5 or the lens L7.

Exceeding the upper limit values of the conditional expressions (5) and (6) is not preferable, because the thickness of the negative (concave) lens L6 becomes excessively small, causing cracking and chipping, or the thicknesses of the positive (convex) lenses L5 and L7 become excessively large and the overall endoscope optical system is increased.

It is desirable that the following conditional expression (5)' be satisfied instead of the conditional expression (5).

$$2.3 < DG31/DG32 < 3 \tag{5}'$$

Furthermore, it is more desirable that the following conditional expression (5)" be satisfied instead of the conditional expression (5).

$$2.5 < DG31/DG32 < 2.6 \tag{5}''$$

It is desirable that the following conditional expression (6)' be satisfied instead of the conditional expression (6).

$$1.5 < DG33/DG32 < 1.8 \tag{6}'$$

Furthermore, it is more desirable that the following conditional expression (6)" be satisfied instead of the conditional expression (6).

$$1.55 < DG33/DG32 < 1.7 \tag{6}''$$

Furthermore, according to a preferable aspect of the present embodiment, the distance between the three-lens cemented lens CL1 in the third lens group G3 and the two-lens cemented lens CL2 in the third lens group G3 is fixed at a time of switching between the normal observation state and the magnified observation state, and it is desirable that the following conditional expression (7) be satisfied:

$$0.02 < DG3Gair/fw < 0.3 \tag{7}$$

where

DG3Gair is the air space between the three-lens cemented lens CL1 in the third lens group G3 and the two-lens cemented lens CL2 in the third lens group G3, and fw is the focal length of the overall endoscope optical system in the normal observation state.

The conditional expression (7) defines an appropriate air space between the three-lens cemented lens CL1 and the two-lens cemented lens CL2 in the third lens group G3.

Within a range of the conditional expression (7), an appropriate air space is obtained. In this case, it is preferable, in particular, because the size of the two-lens cemented lens CL2 is not increased.

When the conditional expression (7) takes a value smaller than the lower limit value thereof, the air space is excessively small and therefore the three-lens cemented lens CL1 and the two-lens cemented lens CL2 come into contact with each other due to frame or lens tolerances. In this case, the lenses may become cracked or broken and therefore this is not preferable.

When the conditional expression (7) takes a value larger than the upper limit value thereof, the air space becomes excessively large and therefore, in particular, the size of the two-lens cemented lens CL2 is increased. In this case, the endoscope optical system becomes excessively large and therefore this is not preferable.

It is desirable that the following conditional expression (7)' be satisfied instead of the conditional expression (7).

$$0.025 < DG3Gair/fw < 0.055 \tag{7}'$$

Furthermore, it is more desirable that the following conditional expression (7)" be satisfied instead of the conditional expression (7).

$$0.04 < DG3Gair/fw < 0.05 \tag{7}''$$

Furthermore, according to a preferable aspect of the present embodiment, it is desirable that all of the lenses in the first lens group G1, the lenses in the second lens group G2, and the lenses in the third lens group G3 be spherical lenses.

It is preferable because the manufacturing cost becomes low owing to spherical lenses.

Furthermore, according to a preferable aspect of the present embodiment, it is desirable that the following conditional expression (8) be satisfied:

$$0.6 < ER3G1/ER3G2 < 0.9 \tag{8}$$

where

ER3G1 is the maximum outer diameter of the three-lens cemented lens CL1 in the third lens group G3, and ER3G2 is the maximum outer diameter of the two-lens cemented lens CL2 in the third lens group G3.

The conditional expression (8) defines an appropriate relation between the three-lens cemented lens CL1 and the two-lens cemented lens CL2 in the third lens group G3.

When the conditional expression (8) takes a value larger than the upper limit value thereof, there is no difference in lens outer diameter. This case is not preferable because it is impossible to have a cementing margin for cementing of the three-lens cemented lens CL1.

Falling below the lower limit value of the conditional expression (8) is not preferable because if so, the two-lens cemented lens CL2 becomes excessively large and the size of the endoscope optical system is increased.

It is desirable that the following conditional expression (8)' be satisfied instead of the conditional expression (8).

$$0.7 < ER3G1/ER3G2 < 0.85 \tag{8}'$$

Example 1

FIG. 1A is a lens sectional view in a normal observation state of an endoscope optical system according to Example 1. FIG. 1B is a lens sectional view in a magnified observation state of the endoscope optical system according to Example 1.

The endoscope optical system includes, in order from an object side: a fixed negative first lens group G1; a movable positive second lens group G2; a fixed aperture stop S; and a fixed positive third lens group G3. An image plane (image pickup surface) is denoted by I.

It is possible to switch between the normal observation state and the magnified observation state by moving the second lens group G2 along the optical axis AX.

The first lens group G1 includes, in order from the object side: a plano-concave negative lens L1 having a flat surface directed toward the object side; a parallel plate F; a biconcave negative lens L2; and a positive meniscus lens L3 having a convex surface directed toward the object side. The negative lens L2 and the positive meniscus lens L3 are cemented.

The second lens group G2 includes a positive meniscus lens L4 having a convex surface directed toward the object side.

The third lens group G3 includes a biconvex positive lens L5, a plano-concave negative lens L6 having a flat surface directed toward the image side, a plano-convex positive lens L7 having a flat surface directed toward the object side, a biconvex positive lens L8, and a negative meniscus lens L9 having a convex surface directed toward the image side. The positive lens L5, the negative lens L6, and the positive lens L7 are cemented to form a cemented lens CL1. The positive lens L8 and the negative meniscus lens L9 are cemented to form a cemented lens CL2.

The aperture stop S is provided between the second lens group G2 and the third lens group G3.

The parallel plate F is, for example, an infrared absorption filter. A coating for cutting off YAG laser and a coating for cutting off LD laser are respectively provided on the object side and the image side of the parallel plate F.

FIG. 3A illustrates spherical aberration (SA) in the normal observation state, FIG. 3B illustrates astigmatism (AS) in the normal observation state, FIG. 3C illustrates distortion (DT) in the normal observation state, and FIG. 3D illustrates chromatic aberration of magnification (CC) in the normal observation state of the endoscope optical system according to Example 1.

FIG. 3E illustrates spherical aberration (SA) in the magnified observation state, FIG. 3F illustrates astigmatism (AS) in the magnified observation state, FIG. 3G illustrates distortion (DT) in the magnified observation state, and FIG. 3H illustrates chromatic aberration of magnification (CC) in the magnified observation state.

Example 2

FIG. 4A is a lens sectional view in a normal observation state of an endoscope optical system according to Example 2. FIG. 4B is a lens sectional view in a magnified observation state of the endoscope optical system according to Example 2.

The endoscope optical system includes, in order from an object side: a fixed negative first lens group G1; a movable positive second lens group G2; a fixed aperture stop S; and a fixed positive third lens group G3. An image plane (image pickup surface) is denoted by I.

It is possible to switch between the normal observation state and the magnified observation state by moving the second lens group G2 along an optical axis AX.

The first lens group G1 includes, in order from the object side: a plano-concave negative lens L1 having a flat surface directed toward the object side; a parallel plate F; a biconcave negative lens L2; and a positive meniscus lens L3 having a convex surface directed toward the object side. The negative lens L2 and the positive meniscus lens L3 are cemented.

The second lens group G2 includes a positive meniscus lens L4 having a convex surface directed toward the object side.

The third lens group G3 includes a biconvex positive lens L5, a plano-concave negative lens L6 having a flat surface directed toward the image side, a plano-convex positive lens L7 having a flat surface directed toward the object side, a biconvex positive lens L8, and a negative meniscus lens L9 having a convex surface directed toward the image side. The positive lens L5, the negative lens L6, and the positive lens L7 are cemented to form a cemented lens CL1. The positive lens L8 and the negative meniscus lens L9 are cemented to form a cemented lens CL2.

The aperture stop S is provided between the second lens group G2 and the third lens group G3.

The parallel plate F is, for example, an infrared absorption filter. A coating for cutting off YAG laser and a coating for cutting off LD laser are respectively provided on the object side and the image side of the parallel plate F.

FIG. 5A illustrates spherical aberration (SA) in the normal observation state, FIG. 5B illustrates astigmatism (AS) in the normal observation state, FIG. 5C illustrates distortion (DT) in the normal observation state, and FIG. 5D illustrates chromatic aberration of magnification (CC) in the normal observation state of the endoscope optical system according to Example 2.

FIG. 5E illustrates spherical aberration (SA) in the magnified observation state, FIG. 5F illustrates astigmatism (AS) in the magnified observation state, FIG. 5G illustrates distortion (DT) in the magnified observation state, and FIG. 5H illustrates chromatic aberration of magnification (CC) in the magnified observation state.

Numerical data of the examples above are described below. In surface data, r represents the radius of curvature of each lens surface, d represents the distance between lens surfaces, nd represents the refractive index of d line of each lens, and vd represents the Abbe number of each lens. (S) represents the aperture stop, fb represents a back focus, f1 represents the focal length of the first lens group G1, f2 represents the focal length of the second lens group G2, and f3 represents the focal length of the third lens group G3.

Example 1

Unit mm
Surface data

| Surface no. | r | d | nd | vd |
|---|---|---|---|---|
| 1 | ∞ | 0.53 | 1.88300 | 40.76 |
| 2 | 1.883 | 1.99 | | |
| 3 | ∞ | 0.61 | 1.49400 | 75.01 |
| 4 | ∞ | 0.50 | | |
| 5 | −13.349 | 0.53 | 1.88300 | 40.76 |
| 6 | 2.161 | 3.13 | 1.84666 | 23.78 |
| 7 | 997.256 | Variable | | |
| 8 | 2.083 | 0.82 | 1.48749 | 70.23 |
| 9 | 2.190 | Variable | | |
| 10 (S) | ∞ | 0.09 | | |
| 11 | 4.050 | 1.14 | 1.63854 | 55.38 |
| 12 | −1.705 | 0.46 | 1.88300 | 40.76 |
| 13 | ∞ | 0.71 | 1.69895 | 30.13 |
| 14 | −3.657 | 0.05 | | |
| 15 | 7.396 | 1.08 | 1.48749 | 70.23 |
| 16 | −3.572 | 0.53 | 1.95906 | 17.47 |
| 17 | −6.112 | Variable | | |
| 18 (Image plane) | ∞ | | | |

Various data

| | Normal observation state | Magnified observation state |
|---|---|---|
| focal length | 1.07 | 1.06 |
| FNO. | 3.57 | 3.53 |
| angle of view 2ω | 141.81 | 138.62 |
| fb (in air) | 4.81 | 4.71 |
| total length (in air) | 19.32 | 19.22 |

-continued

| | | |
|---|---|---|
| d7 | 0.47 | 1.26 |
| d9 | 1.87 | 1.08 |
| d17 | 4.89 | 4.89 |

Unit focal length

| | | |
|---|---|---|
| f1 = −1.49 | f2 = 24.85 | f3 = 3.80 |

Example 2

Unit mm
Surface data

| Surface no. | r | d | nd | vd |
|---|---|---|---|---|
| 1 | ∞ | 0.53 | 1.88300 | 40.76 |
| 2 | 1.846 | 0.74 | | |
| 3 | ∞ | 0.61 | 1.49400 | 75.01 |
| 4 | ∞ | 0.50 | | |
| 5 | −20.951 | 0.53 | 1.88300 | 40.76 |
| 6 | 1.917 | 4.24 | 1.84666 | 23.78 |
| 7 | 32.435 | Variable | | |
| 8 | 2.166 | 1.06 | 1.48749 | 70.23 |
| 9 | 2.283 | Variable | | |
| 10 (S) | ∞ | 0.09 | | |
| 11 | 3.975 | 1.14 | 1.63854 | 55.38 |
| 12 | −1.625 | 0.46 | 1.88300 | 40.76 |
| 13 | ∞ | 0.71 | 1.69895 | 30.13 |
| 14 | −3.536 | 0.05 | | |
| 15 | 7.141 | 1.08 | 1.48749 | 70.23 |
| 16 | −4.085 | 0.52 | 1.95906 | 17.47 |
| 17 | −6.594 | Variable | | |
| 18 (Image plane) | ∞ | | | |

Various data

| | Normal observation state | Magnified observation state |
|---|---|---|
| focal length | 1.06 | 1.06 |
| FNO. | 3.57 | 3.53 |
| angle of view 2ω | 141.85 | 137.25 |
| fb (in air) | 4.65 | 4.55 |
| total length (in air) | 19.55 | 19.45 |
| d7 | 0.96 | 1.75 |
| d9 | 1.69 | 0.90 |
| d17 | 4.72 | 4.72 |

Various focal length

| | | |
|---|---|---|
| f1 = −1.48 | f2 = 21.78 | f3 = 3.69 |

Values of conditional expressions of each examples are shown below:

Conditional Expression $$(nd3G1 + nd3G2 + nd3G3)/3 \quad (1)$$

$$(nd3G4 + nd3G5)/2 \quad (2)$$

$$\omega(\text{wide})/\omega(\text{tele}) \quad (3)$$

$$(R3G3\text{front} + R3G3\text{rear})/(R3G3\text{front} - R3G3\text{rear}) \quad (4)$$

$$DG31/DG32 \quad (5)$$

$$DG33/DG32 \quad (6)$$

$$DG3\text{Gair}/fw \quad (7)$$

$$ER3G1/ER3G2 \quad (8)$$

| Conditional Expression | Example 1 | Example 2 |
|---|---|---|
| (1) | 1.740 | 1.740 |
| (2) | 1.723 | 1.723 |
| (3) | 1.023 | 1.034 |
| (4) | 1.0 | 1.0 |
| (5) | 2.50 | 2.50 |
| (6) | 1.57 | 1.57 |
| (7) | 0.900 | 0.818 |
| (8) | 0.046 | 0.046 |

As described above, the present disclosure is suitable for an endoscope optical system, an endoscope, an image pickup unit, and an endoscope insertion device, in which chromatic aberration is favorably corrected and it is possible to prevent a shift of lenses due to low impact.

According to the present disclosure, it is possible to provide an endoscope optical system, an endoscope, an image pickup unit, and an endoscope insertion device, in which chromatic aberration is favorably corrected and it is possible to prevent a shift of lenses due to low impact.

What is claimed is:

1. An endoscope optical system comprising, in order from an object side:
 a fixed negative first lens group;
 a movable positive second lens group;
 a fixed aperture stop; and
 a fixed positive third lens group,
 wherein:
 the endoscope optical system is configured to switch between a normal observation state and a magnified observation state by moving the second lens group along an optical axis,
 the third lens group consists of, in order from the object side: a cemented lens consisting of three lenses; and a cemented lens consisting of two lenses,
 in the cemented lens consisting of three lenses, three lenses of a positive lens, a negative lens, and a positive lens are cemented,
 the cemented lens consisting of three lenses has a biconvex lens component shape,
 in the cemented lens consisting of two lenses, two lenses of a positive lens and a negative lens are cemented, and
 the following conditional expressions (1) and (2) are satisfied:

$$1.70 < (nd3G1 + nd3G2 + nd3G3)/3 < 2.0 \quad (1), \text{ and}$$

$$1.72 < (nd3G4 + nd3G5)/2 < 2.0 \quad (2),$$

where:
 nd3G1 is a refractive index in d line of a lens nearest to the object side in the cemented lens consisting of three lenses,
 nd3G2 is a refractive index in d line of a lens second nearest to the object side in the cemented lens consisting of three lenses,
 nd3G3 is a refractive index in d line of a lens nearest to an image side in the cemented lens consisting of three lenses, nd3G4 is a refractive index in d line of a lens nearest to the object side in the cemented lens consisting of two lenses, and nd3G5 is a refractive index in d line of a lens nearest to the image side in the cemented lens consisting of two lenses.

2. The endoscope optical system according to claim 1, wherein the following conditional expression (3) is satisfied:

$$1.01<\omega(wide)/\omega(tele)<5.0 \qquad (3),$$

where:

ω(wide) is a half angle of view in the normal observation state of the endoscope optical system, and ω(tele) is a half angle of view in the magnified observation state of the endoscope optical system.

3. The endoscope optical system according to claim 1, wherein the following conditional expression (4) is satisfied:

$$0.8<(R3G3front+R3G3rear)/(R3G3front-R3G3rear)<1.2 \qquad (4),$$

where:

R3G3front is a radius of curvature of an object-side surface of the lens nearest to the image side in the cemented lens consisting of three lenses, and R3G3rear is a radius of curvature of an image-side surface of the lens nearest to the image side in the cemented lens consisting of three lenses.

4. The endoscope optical system according to claim 1, wherein both of the following conditional expressions (5) and (6) are satisfied:

$$2.0<DG31/DG32<3.5 \qquad (5)$$

$$1.4<DG33/DG32<1.9 \qquad (6)$$

where:

DG31 is a lens center thickness of the lens nearest to the object side in the cemented lens consisting of three lenses, DG32 is a lens center thickness of the lens second nearest to the object side in the cemented lens consisting of three lenses, and DG33 is a lens center thickness of the lens nearest to the image side in the cemented lens consisting of three lenses.

5. The endoscope optical system according to claim 1, wherein:

a distance between the cemented lens consisting of three lenses and the cemented lens consisting of two lenses is fixed at a time of switching between the normal observation state and the magnified observation state, and the following conditional expression (7) is satisfied:

$$0.02<DG3Gair/fw<0.3 \qquad (7)$$

where:

DG3Gair is an air space between the cemented lens consisting of three lenses and the cemented lens consisting of two lenses in the third lens group, and fw is a focal length of the overall endoscope optical system in the normal observation state.

6. The endoscope optical system according to claim 1, wherein all of lenses in the first lens group, lenses in the second lens group, and lenses in the third lens group are spherical lenses.

7. The endoscope optical system according to claim 1, wherein the following conditional expression (8) is satisfied:

$$0.6<ER3G1/ER3G2<0.9 \qquad (8)$$

where:

ER3G1 is a maximum outer diameter of the cemented lens consisting of three lenses, and ER3G2 is a maximum outer diameter of the cemented lens consisting of two lenses.

8. An endoscope comprising the endoscope optical system according to claim 1.

9. An image pickup unit comprising:

the endoscope optical system according to claim 1; and an image pickup element configured to pick up an image formed by the endoscope optical system.

10. An endoscope insertion device comprising the image pickup unit according to claim 9 at a distal end thereof.

* * * * *